United States Patent [19]

Ito

[11] Patent Number: 5,763,711

[45] Date of Patent: Jun. 9, 1998

[54] CATALYST FOR THE REARRANGEMENT OF ALLYLIC GEMINAL DIHALOGEN COMPOUNDS

[75] Inventor: Larry N. Ito, Midland, Mich.

[73] Assignee: The Dow Chemical Company, Midland, Mich.

[21] Appl. No.: 691,199

[22] Filed: Aug. 7, 1996

[51] Int. Cl.$^6$ .................................................. C07C 21/09
[52] U.S. Cl. ............................................................ 570/236
[58] Field of Search ............................................. 570/236

[56] References Cited

U.S. PATENT DOCUMENTS 5,072,063  12/1991  Langensee .............................. 570/236
5,510,546  4/1996   Ito ......................................... 570/236

*Primary Examiner*—Paul F. Shaver

[57] ABSTRACT

A process for converting 3,3-dichloropropene in an intermediate boiling byproduct stream from a process of making allyl chloride by the chlorination of propylene to cis- or trans-1,3-dichloropropene or a mixture of these, wherein the 3,3-dichloropropene is contacted in the liquid phase with an alumina, silica or zeolite catalyst, characterized in that the alumina, silica or zeolite catalyst is selected to possess a predominance of basic sites as associated with a high alkali or alkaline earth metals content, for increased conversion and productivity and reduced catalyst deactivation rates.

26 Claims, No Drawings

CATALYST FOR THE REARRANGEMENT OF ALLYLIC GEMINAL DIHALOGEN COMPOUNDS

BACKGROUND OF THE INVENTION

A significant by-product in the important commercial process of producing allyl chloride through the chlorination of propylene is 3,3-dichloropropene. Unfortunately, 3,3-dichloropropene and its homologs do not have a significant commercial use, so that the 3,3-dichloropropene produced in this manner has heretofore usually been incinerated.

As related in U.S. Pat. No. 5,072,063 to Langensee (hereafter, "Langensee"), a number of efforts have been made at the same time to produce the 1,3-dichloropropenes also produced as byproducts in the allyl chloride process, because of the known utility of both the cis- and trans-isomers of 1,3-dichloropropene as, for example, nematocides (German Patent Application No. 1,210,618), soil fumigants, insecticides and monomers in the production of plastics, resins and chemical intermediates.

These past efforts have included reacting 1,2-dichloropropane with a gas containing oxygen in the presence of a catalyst containing $CuCl_2$, $LiCl$ and $ZnCl_2$ at 470 to 490 degrees Celsius, dehydrochlorination of 1,2,3-trichloropropane in the presence of oxygen or halogen, contacting 1,2-dichloropropane with chlorine to effect both chlorination and dechlorination reactions, or mixing 1,2-dichloropropane with allyl chloride and/or 1-chloropropene and reacting with chlorine at high temperature.

Langensee elected, in view of the availability and lack of utility of 3,3-dichloropropene and further citing the complicated, energy-consuming and/or inconvenient nature of the aforementioned processes, to pursue the isomerization of a 3,3-dihalopropene generally and 3,3-dichloropropene more particularly to the respective 1,3-dihalopropenes or 1,3-dichloropropenes and homologs thereof. This isomerization was accomplished by contacting the 3,3-dichloropropene with an alumina, silica or zeolite catalyst, and especially an alumina, silica or zeolite having acidic sites, in preferably a fixed bed, continuous process. In particular, Langensee contemplated the isomerization would be conducted directly on a 3,3-dichloropropene-containing byproduct stream from a distillation of the product stream from an allyl chloride process, to produce cis- and trans-1,3-dichloropropenes to be combined with the cis- and trans-1,3-dichloropropenes otherwise produced in the allyl chloride process and recovered through distillation.

An earlier Japanese patent, JP 80-69,523, was cited for also teaching an isomerization process, involving contacting 3,3-dichloropropene in the presence of hydrogen chloride with a catalytic amount of a zinc, iron, copper, tin, titanium or vanadium salt at between 0 degrees and 200 degrees Celsius. The difficulty found by Langensee with respect to the Japanese process, however, was that the catalyst was suspended in the reaction mixture and difficult to remove from the reaction mixture after completion of the rearrangement process.

SUMMARY OF THE INVENTION

The present invention provides a significant further improvement on the isomerization processes taught in Langensee and the earlier Japanese patent, and comprises a process for preparing the 1,3-dichloropropenes, such as cis- and trans-1,3-dichloropropene, and their homologs or the 1,3-dibromopropenes from 3,3-dichloropropene or 3,3-dibromopropene, respectively.

The process of the present invention utilizes an alumina, silica or zeolite which is characterized as having a predominance of basic, as opposed to acidic, sites therein as associated with a high alkali or alkaline earth metals content, such aluminas, silicas and zeolites having been found to have unexpectedly superior lifetimes and productivities for the preferred isomerization of 3,3-dichloropropene to the useful 1,3-dichloropropenes as compared to the acidic aluminas, silicas and zeolites described and strongly favored by Langensee.

Further, and contrary to Langensee's teachings, there appears to be value in the context of the process of the present invention to conducting the process at higher temperatures. Langensee broadly teaches an isomerization process which is conducted at temperatures ranging from 0 degrees Celsius to 130 degrees Celsius, but prefers temperatures of from 20 degrees Celsius to 120 degrees Celsius, and especially prefers temperatures from 50 degrees Celsius to 110 degrees Celsius. The present, improved process is preferably conducted at elevated temperatures of from about 120 degrees Celsius up to the degradation temperature of 1,3-dichloropropene, but more preferably is conducted at temperatures in excess of about 130 degrees Celsius and most preferably is conducted at temperatures of about 140 degrees Celsius and perhaps still higher temperatures.

DETAILED DESCRIPTION OF PREFERRED EMBODIMENTS

Without being limiting of the present invention, it is theorized that the higher rates of deactivation observed below in an unmodified, acidic alumina, for example, may be attributed to an acid site-catalyzed polymerization of unsaturated chlorinated hydrocarbons in the allyl chloride byproduct stream, and that an exchange of sodium cations (or alkali or alkaline earth metals, more generally) at the acid sites makes these sites ineffective for such polymerization. Accordingly, the effect of exchanging alkali or alkaline earth metals at the acid sites of Langensee's favored, acidic alumina, silica or zeolite catalysts is expected to be most pronounced for the aluminas and zeolites as these are generally the more acidic of the three classes of materials, and less pronounced but still significant with the typically less-acidic silicas.

The materials to be isomerized by the present process are of the general Formula I as follows:

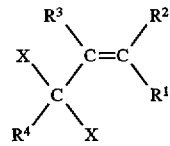

wherein X represents chloro and $R^1$, $R^2$, $R^3$ and $R^4$ independently represent hydrogen or a $C_1$–$C_3$ straight chain or branched chain alkyl group (for example, methyl, ethyl, propyl and 1-methylethyl), or wherein X is bromo and each of $R^1$, $R^2$, $R^3$, and $R^4$ is hydrogen.

Compounds of this Formula I wherein X is chloro and $R^1$, $R^2$, $R^3$ and $R^4$ independently are hydrogen or a methyl group are preferred, as are compounds wherein each of $R^1$, $R^2$, $R^3$ and $R^4$ are hydrogen. Isomerization of 3,3-dichloropropene (3,3-DCPe) is again especially of interest, such material being conventionally contained in an intermediate boiling point by-product fraction from the distillation of the product stream from a process of making allyl chloride by the chlorination of propylene, for example as disclosed in U.S.

Pat. No. 4,319,062 to Boozalis et al., the teaching of which are incorporated by reference.

The intermediate boiling fraction that remains after removing a lower boiling fraction containing the desired allyl chloride product from such a process, and after removing higher boiling fractions containing most of the cis- and trans-1,3-dichloropropenes, includes a variety of chlorinated propanes and propenes of which generally between about 10 and about 20 percent by total weight is the targeted 3,3-dichloropropene. Other byproducts of the allyl chloride process include the just-mentioned cis- and trans-1,3-dichloropropenes, 2,3-dichloropropene, 2,2-dichloropropane, 1,2-dichloropropane and related species, with 1,2-dichloropropane being present generally as a major component at from approximately 50 percent to about 85 percent by weight, and typically being present at from about 60 to about 75 percent by weight.

The products of the isomerization process of the present invention in a general sense are the corresponding dichloroalkenes or dibromoalkenes of Formula II or Formula III:

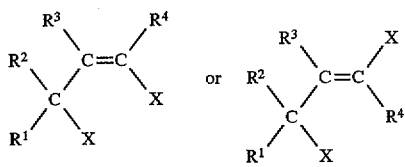

wherein X is chloro and $R^1$, $R^2$, $R^3$ and $R^4$ independently are hydrogen or a $C_1$-$C_3$ straight chain or branched chain alkyl group, or X is bromo and each of $R^1$, $R^2$, $R^3$ and $R^4$ is hydrogen. Within this class of products, compounds wherein X is chloro and $R^1$, $R^2$, $R^3$ and $R^4$ independently are hydrogen or a methyl group are preferred, as are compounds wherein each of $R^1$, $R^2$, $R^3$ and $R^4$ is hydrogen. 1,3-Dichloropropene in either the cis- or trans-configuration is especially preferred as a product, corresponding to Formulas II and III, respectively, wherein X is chloro and each of $R^1$, $R^2$, $R^3$ and $R^4$ is hydrogen. Generally, some of both isomers is produced, and the present invention contemplates the production of either of these isomers or a mixture of these.

As has been indicated, a most preferred process embodiment will involve chlorinating propylene according to any conventional process for producing allyl chloride, then distilling the product stream to provide an intermediate boiling byproduct stream containing the 3,3-dichloropropene. Thereafter, the intermediate boiling byproduct stream containing 3,3-dichloropropene and what is in effect an inert chlorocarbon diluent is exposed to an alumina, silica or zeolite catalyst which is preferably characterized by particle sizes in the range of from about 0.5 inches (12.5 mm) in diameter to about 100 mesh (0.15 mm), and which has an alkali or alkaline earth metals content associated with a basic character in an aqueous slurry of the alumina, silica or zeolite, typically being from about 0.1 weight percent to about 10 weight percent on an elemental basis. More preferably, the alumina, silica or zeolite is characterized by a particle size of from about 6 mesh (3.4 mm) to about 40 mesh (0.4 mm), and most preferably is characterized by a particle size of from about 10 mesh (2 mm), and especially about 14 mesh (1.4 mm), down to about 20 mesh (0.8 mm). A preferred alkali or alkaline earth metals content is from about 0.2 weight percent to about 5 weight percent, and most preferably the alkali or alkaline earth metal content of the catalyst will be from about 0.3 weight percent to about 2 weight percent.

Aluminas, silicas and zeolites are commercially available with various alkali metal contents, but with respect to the activated aluminas at least, those activated aluminas which are derived from Bayer process gibbsite, α-Al(OH)$_3$, or unrefined bauxite (containing as much as 90 percent of gibbsite on a dry basis) and which are characterized by comparatively higher amounts of sodium oxide (Na$_2$O) as an impurity (for example about 0.2 to 0.3 weight percent of Na$_2$O for gibbsite on a Al(OH)$_3$ basis) have been less favored for catalytic use (Kirk-Othmer, Encyclopedia of Chemical Technology, Vol. 2, "Aluminum Compounds (Activated)", 4th ed. (1995)), although apparently promoting aluminas with a "small amount" of alkali has been found beneficial in at least one other catalytic context, in certain Claus operations (Kirk-Othmer, citing a brochure, "SP-100 Promoted Activated Alumina for Claus Catalysis", Alcoa Chemicals Division, Aluminum Company of America, Pittsburgh, Pa. 1984). Aluminas with higher sodium oxide contents are consequently and advantageously inexpensive, and for this reason are especially preferred for use in the present invention. Aluminas which do not have the desired amounts of alkali or alkaline earth metals in their commercially-available forms may be impregnated with an aqueous solution of NaOH, for example, as an easy, inexpensive way of achieving the sodium/alkali metal content and consequent basic character desired in the process of the present invention.

Suitable commercially-available, basic aluminas which have been identified include Rhone Poulenc's SAS-350 activated alumina (Rhone Poulenc Inc., having a pH in aqueous slurry of about 9.3 and a sodium content of 0.6 weight percent on an elemental basis), Alcoa's F1 grade alumina (Aluminum Company of America, Pittsburgh, Pa.; not calcined/activated, having a pH in aqueous slurry of about 9.98 and a sodium content of 0.35 weight percent), Alcoa's F200 grade alumina (Aluminum Company of America, Pittsburgh, Pa.; not calcined/activated, having a pH in aqueous slurry of about 10.05 and a sodium content of 0.18 percent by weight), and Alcoa's DD2 grade alumina (having a pH in aqueous slurry of about 9.94). These are preferably ground and sieved as appropriate to be of the preferred particle sizes for use in the present invention.

Other than the departures from Langensee which have been discussed already (that is, in the selection of an alumina, silica or zeolite catalyst having a certain particle size and a certain alkali or alkaline earth metals content, and in terms of temperatures employed in the process), the process of the present invention can be satisfactorily carried out according to Langensee's teachings. Thus, the contemplated isomerization process can be carried out batchwise or continuously, with a fixed bed, continuous process being preferred but a fluidized bed process also being possible.

Any pressure can be used, but preferably the pressure and temperature are selected so that substantially all of the components of the byproduct stream fed to the isomerization process remain in the liquid state, exemplary pressures being from ambient pressure up to about 1500 kPa. Reaction times can vary with the starting material to be isomerized, the process temperature, catalyst and reactor type employed. Exemplary batch times for a batchwise process range from about 0.5 to about 8 hours, generally falling in the range of from about 1.5 to about 4 hours. A fixed bed residence time in a continuous process of from 1 to 300 minutes is considered generally sufficient, with times of from about 2 to about 180 minutes, and especially from about 2 to about 120 minutes being preferred.

Where the 3,3-DCPe-containing, intermediate boiling byproduct stream is not processed directly through the isomerization process of the present invention, but is stored, transported or otherwise placed in an environment wherein the material may acquire water, then preferably the 3,3-DCPe-containing feed is first dried by any conventional means or method for accomplishing this end. In this regard, it has been found that water such as may be acquired by the feed material in storage or through other means has a significantly adverse impact on the rate of deactivation and productivity seen in further processing the stream according to the process described herein. Thus, the 3,3-DCPe-containing feed is preferably dried to a water content of less than about 50 parts per million by weight, but more preferably is dried to a water content of less than about 30 parts per million and most preferably about 15 parts per million by weight or less of water.

The drying step can again be performed by any known means or according to any known method for doing so, a preferred, exemplary means or method involving passing the byproduct stream over molecular sieves or other water-absorbing materials conventionally used in drying applications at essentially ambient temperatures.

The present invention is more particularly illustrated by the Examples which follow:

ILLUSTRATIVE EXAMPLES

Example 1

An acidic activated alumina (pH of 6.54 in aqueous slurry, about 0.01 weight percent of sodium) sold by Norton Chemical Process Products with the designation SA-6275 was ground and sieved to a 14 by 20 mesh (1.4 mm by 0.85 mm), and impregnated with NaOH from aqueous solution to a sodium content of approximately 0.30 weight percent, on an elemental basis). The sodium-promoted alumina was then evaluated by passing 6.0 ml per hour of the 3,3-dichloropropene-containing, intermediate boiling fraction from a distillation of the products of a commercial allyl chloride process over 5.0 cubic centimeters of the alumina catalyst in a 316 stainless steel, 0.5 inch (12.7 mm) O.D. liquid phase tubular reactor maintained at 130 pounds per square inch, gauge (0.9 MPa, gauge) and 120 degrees Celsius. The maximum conversion observed of 3,3-dichloropropene to the cis- and trans-isomers of 1,3-dichloropropene was 99.1 percent, with an apparent deactivation rate of 0.00025 percent per hour and a productivity of 9,114 grams 3,3-DCPe (3,3-dichloropropene) converted per gram of the sodium-promoted alumina catalyst.

Comparative Examples 1 and 2

For comparison, the same Norton SA-6275, acidic activated alumina was ground and sieved as in Example 1, and evaluated without being impregnated from an aqueous NaOH solution. All other conditions being the same, at a temperature of 90 degrees Celsius the maximum conversion observed was again at 99.1 percent, but the deactivation rate was 0.088 percent per hour and the productivity was 25.9 grams 3,3-DCPe converted per gram of catalyst. At a temperature of 120 degrees Celsius, the maximum conversion was 98.9 percent, the deactivation rate was 0.024 percent per hour, and the catalyst productivity was determined to be 94.9 grams of 3,3-DCPe converted per gram of catalyst.

Examples 2 and 3

A basic alumina discussed and characterized above, grade SAS-350 activated alumina from Rhone Poulenc Inc., was ground and sieved to a 14 by 20 mesh (1.4 mm by 0.85 mm) and evaluated as in Example 1, at temperatures of 90 degrees Celsius and 120 degrees Celsius. At 90 degrees Celsius, the maximum conversion observed of 3,3-DCPe to 1,3-DCPe was 98.3 percent, with a deactivation rate of 0.00318 percent per hour and a productivity of 711 grams 3,3-DCPe converted per gram of catalyst. At 120 degrees Celsius, the maximum conversion was 98.8 percent, with a deactivation rate of 0.00127 percent per hour and with 1790 grams of 3,3-DCPe being isomerized per gram of catalyst.

Comparative Example 3

For comparison to the results seen in Examples 2 and 3, and to illustrate the significance of particle size in the context of the exemplified process, a Rhone Poulenc grade SAS-350 activated alumina in the form of 3/16 inch (4.8 mm) spheres was evaluated at 120 degrees Celsius. The maximum conversion observed was 80.0 percent, with a deactivation rate of 0.038 percent per hour and a productivity of 23.5 grams 3,3-DCPe isomerized per gram of catalyst.

Example 4

A basic, uncalcined Alcoa grade F1 alumina in an 8 by 14 mesh particle size was evaluated at 120 degrees Celsius in the manner of Examples 1–3. The maximum conversion was 99.1 percent, with a deactivation rate of 0.00123 percent per hour and a productivity of 1850 grams of 3,3-DCPe converted per gram of catalyst.

Examples 5 and 6

A basic Alcoa DD2 grade alumina was ground and sieved to a 14×20 mesh size, and evaluated as in previous examples with a predried (with molecular sieves, to 15 ppm of water) feed at 90 degrees Celsius and 120 degrees Celsius. At 90 degrees, the maximum conversion was 98.5 percent, with a deactivation rate of 0.00324 percent per hour and a productivity of 698 grams of 3,3-DCPe converted per gram of alumina catalyst. At 120 degrees Celsius, the maximum conversion was 99.2 percent, the observed deactivation rate was 0.000926 percent per hour and the productivity was determined to be 2,460 grams of 3,3-DCPe converted per gram of catalyst.

Examples 7 and 8

An acidic alumina from Calsicat (grade SB, having a pH in aqueous solution of 6.51 in an unimpregnated condition and being ground and sieved to a 14×20 mesh size) was impregnated with NaOH from an aqueous solution thereof to a sodium content of approximately 0.30 weight percent (on an elemental basis) and a pH of 10.35 in aqueous solution, and evaluated at 90 and 120 degrees Celsius. At 90 degrees Celsius, the maximum conversion was found to be 97.9 percent, with an observed deactivation rate of 0.0172 percent per hour and a productivity of 131 grams of 3,3-DCPe per gram of catalyst. At 120 degrees, the maximum conversion was 98.6 percent, the deactivation rate was 0.00491 percent per hour and the catalyst productivity was 461 grams of 3,3-DCPe feed converted per gram of catalyst.

Comparative Examples 4 and 5

The same acidic alumina as employed in Examples 7 and 8 was run in an unimpregnated condition, with the result that at 90 degrees Celsius, the maximum conversion was 97.6 percent, with a deactivation rate of 0.321 percent per hour and a productivity of 6.99 grams of 3,3-DCPe converted per gram of catalyst. At 120 degrees Celsius, the maximum conversion was 98.4 percent, the deactivation rate was 0.0943 percent per hour and the productivity was found to be 23.9 grams of 3,3-DCPe converted per gram of catalyst.

Examples 9 and 10

An acidic alumina from Norton Chemical Process Products (grade "9316079", with a pH in aqueous solution of 6.59 and being ground and sieved to a 14×20 mesh particle size) was impregnated with an aqueous solution of NaOH to a sodium content of approximately 0.30 weight percent, and to a pH in aqueous solution of 10.14. The impregnated catalyst was tested as in previous examples, at 90 degrees Celsius and 120 degrees Celsius. At 90 degrees Celsius, the maximum conversion was 97.5 percent, with a deactivation rate of 0.0836 percent conversion loss per hour and a productivity of 26.8 grams of 3,3-DCPe converted per gram of catalyst. At 120 degrees, the maximum conversion was found to be 98.4 percent, with a deactivation rate of 0.0246 percent per hour and a productivity of 91.8 grams of 3,3-DCPe converted per gram of catalyst.

Comparative Examples 6 and 7

The same acidic alumina as employed in Examples 9 and 10 was run at 90 and 120 degrees Celsius, in an unimpregnated, acidic condition. At 90 degrees Celsius, the maximum conversion was 91.1 percent, the deactivation rate was considerably higher at 1.58 percent conversion loss per hour, and the productivity was 1.32 grams of 3,3-DCPe converted per gram of catalyst. At 120 degrees, the maximum conversion was 92.9 percent, the deactivation rate (DR in Table 1 below) was 0.451 percent conversion loss per hour and the productivity was 4.72 grams of 3,3-DCPe converted per gram of catalyst.

The results from examples 1–10 and Comparative Examples 1–7 are grouped and tabulated in Table 1 as follows:

TABLE I

| Catalyst | T (°C.) | Max. Conv. (%) | DR (%/hr) | Prod.(a) |
| --- | --- | --- | --- | --- |
| Norton 6275 | 90 | 99.1 | 0.088 | 25.9 |
|  | 120 | 98.9 | 0.024 | 94.9 |
| (Na⁺ added) | 120 | 99.1 | 0.00025 | 9114 |
| R-P SAS-350, ³⁄₁₆"spheres | 120 | 80.0 | 0.038 | 23.5 |
| SAS-350, 14 × 20 mesh | 90 | 98.3 | 0.00318 | 711 |
|  | 120 | 98.8 | 0.00127 | 1790 |
| Alcoa F-1 | 120 | 99.1 | 0.00123 | 1850 |
| Alcoa DD2 | 90 | 98.5 | 0.00324 | 698 |
|  | 120 | 99.2 | 0.000926 | 2460 |
| Calsicat SB | 90 | 97.6 | 0.321 | 6.99 |
|  | 120 | 98.4 | 0.0943 | 23.9 |
| (Na⁺ added) | 90 | 97.9 | 0.0172 | 131 |
|  | 120 | 98.6 | 0.00491 | 461 |
| Norton 9316079 | 90 | 91.1 | 1.58 | 1.32 |
|  | 120 | 92.9 | 0.451 | 4.72 |
| (Na⁺ added) | 90 | 97.5 | 0.0836 | 26.8 |
|  | 120 | 98.4 | 0.0246 | 91.8 |

(a)Productivity in grams of 3,3-DCPe converted per gram of catalyst;

As can be seen particularly from a comparison of the results for the acidic aluminas tested in a conventional, unimpregnated condition and in a sodium-impregnated, basic condition, the basic versions of these aluminas exhibited surprisingly lower rates of deactivation and much higher productivities than the acidic versions favored by Langensee. For example, for the Norton 6275 grade alumina, at 120 degrees the deactivation rate of the acidic alumina was 96 times greater than for the sodium-impregnated, basic alumina formed therefrom. For the Calsicat SB grade alumina, the acidic, unimpregnated alumina deactivated 18.7 times as fast as the basic version at 90 degrees and 19.2 times as fast at 120 degrees Celsius. With respect to the Norton 9316079 grade alumina, the acidic alumina deactivated about 18.9 times as fast as the basic alumina formed therefrom at 90 degrees Celsius, and about 18.3 times as fast at 120 degrees Celsius.

I claim:

1. A process for preparing a dihaloalkene compound of the formula

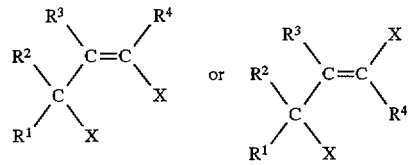

wherein

X represents chloro or bromo $R^1$, $R^2$, $R^3$, and $R^4$ independently represent hydrogen or a $C_1$–$C_3$ alkyl group, with the proviso that when X represents bromo each of $R^1$, $R^2$, $R^3$, and $R^4$ represents hydrogen or a mixture of such compounds, which process comprises contacting a dihaloalkene compound of the formula

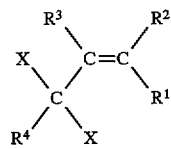

wherein

X represents chloro or bromo and $R^1$, $R^2$, $R^3$, and $R^4$ independently represent hydrogen or a $C_1$–$C_3$ alkyl group with the proviso that when X represents bromo each of $R^1$, $R^2$, $R^3$, and $R^4$ represents hydrogen in the liquid state with an alumina, silica or zeolite catalyst under conditions effective to carry out the conversion, characterized in that the catalyst possesses a predominance of basic sites therein.

2. A process as defined in claim 1, wherein the dihaloalkene compound contacted with the catalyst is 3,3-dichloropropene.

3. A process as defined in claim 2, wherein the 3,3-dichloropropene starting material is a component of an intermediate boiling byproduct stream derived from the distillation of the products of a process for making allyl chloride by the chlorination of propylene.

4. A process as defined in claim 3, wherein cis- or trans-1,3-dichloropropene or a mixture of these are produced from the 3,3-dichloropropene in the intermediate boiling byproduct stream.

5. A process as defined in claim 4, wherein the catalyst has an alkali metal or alkaline earth metals content of from about 0.1 weight percent to about 10 weight percent on an elemental basis.

6. A process as defined in claim 5, wherein the catalyst is characterized by a particle size in the range of from about 0.4 mm to about 3.4 mm and as having an alkali or alkaline earth metals content of from 0.2 about weight percent to 5 about weight percent.

7. A process as defined in claim 6, wherein the catalyst is characterized by a particle size in the range of from about 0.8 mm to about 2.0 mm and as having an alkali or alkaline earth metals content of from about 0.3 weight percent to about 2 weight percent.

8. A process as defined in claim 4, wherein the process is conducted at elevated temperatures in excess of about 120 degrees Celsius.

9. A process as defined in claim 8, wherein the process is conducted at elevated temperatures in excess of about 130 degrees Celsius.

10. A process as defined in claim 9, wherein the process is conducted at elevated temperatures of about 140 degrees Celsius or greater.

11. A process as defined in claim 1, wherein the process is conducted with a fixed bed in a continuous manner.

12. A process as defined in claim 1, wherein the catalyst is a basic alumina having a particle size in the range of from about 0.4 mm to about 3.4 mm and having an alkali or alkaline earth metals content of from 0.2 about weight percent to about 5 weight percent.

13. A process as defined in claim 12, wherein the catalyst is a basic, non-activated alumina having a particle size in the range of from about 0.8 mm to about 2 mm and having an alkali or alkaline earth metals content of from 0.3 about weight percent to about 2 weight percent.

14. A process as defined in claim 1, wherein the catalyst is a basic, non-activated alumina.

15. A process for preparing cis- or trans-1,3-dichloropropene or a mixture of these, which comprises contacting 3,3-dichloropropene in the liquid state with an alumina, silica or zeolite catalyst which is characterized by an alkali or alkaline earth metals content of from about 0.1 weight percent to about 10 weight percent, under conditions effective to carry out the conversion.

16. A process as defined in claim 15, wherein the 3,3-dichloropropene starting material is a component of an intermediate boiling byproduct stream derived from the distillation of the products of a process for making allyl chloride by the chlorination of propylene, the intermediate boiling byproduct stream being additionally comprised of an inert chlorocarbon diluent which is 1,2-dichloropropane or a mixture of chlorinated hydrocarbons, of which 1,2-dichloropropane is a predominant portion.

17. A process as defined in claim 16, wherein the catalyst has a particle size in the range of from about 0.15 mm to about 12.5 mm.

18. A process as defined in claim 17, wherein the catalyst is characterized by a particle size in the range of from about 0.4 mm to about 3.4 mm and as having an alkali or alkaline earth metals content of from about 0.2 weight percent to about 5 weight percent.

19. A process as defined in claim 18 wherein the catalyst is characterized by a particle size in the range of from about 0.8 mm to about 2.0 mm and as having an alkali or alkaline earth metals content of from about 0.3 weight percent to about 2 weight percent.

20. A process as defined in claim 15, wherein the process is conducted at elevated temperatures in excess of about 120 degrees Celsius.

21. A process as defined in claim 20, wherein the process is conducted at elevated temperatures in excess of about 130 degrees Celsius.

22. A process as defined in claim 21, wherein the process is conducted at elevated temperatures of about 140 degrees Celsius or greater.

23. A process as defined in claim 15, wherein the process is conducted with a fixed bed in a continuous manner.

24. A process as defined in claim 15, wherein the catalyst is a basic alumina having a particle size in the range of from about 0.4 mm to about 3.4 mm and having an alkali or alkaline earth metals content of from about 0.2 weight percent to about 5 weight percent.

25. A process as defined in claim 24, wherein the catalyst is a basic, non-activated alumina having a particle size in the range of from about 0.8 mm to about 2.0 mm and having an alkali or alkaline earth metals content of from about 0.3 weight percent to about 2 weight percent.

26. A process as defined in claim 15, wherein the catalyst is a basic, non-activated alumina.

* * * * *